(12) United States Patent
Ota et al.

(10) Patent No.: US 6,312,423 B1
(45) Date of Patent: Nov. 6, 2001

(54) LASER TREATMENT APPARATUS

(75) Inventors: Yasuo Ota, Gamagori; Tokio Ueno, Nagoya, both of (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/317,108

(22) Filed: May 24, 1999

(30) Foreign Application Priority Data

| May 28, 1998 | (JP) | ................................................. 10-146892 |
| Apr. 2, 1999 | (JP) | ................................................. 11-096555 |
| May 10, 1999 | (JP) | ................................................. 11-128461 |

(51) Int. Cl.[7] ................................................. A61F 9/008
(52) U.S. Cl. ................................. 606/4; 606/10; 606/13; 351/206; 351/213
(58) Field of Search ............................... 606/4–6, 10, 11, 606/13, 16, 17; 351/206, 209, 211, 215

(56) References Cited

U.S. PATENT DOCUMENTS

| 4,477,159 | * | 10/1984 | Mizuno et al. . |
| 4,484,797 | | 11/1984 | Knop et al. . |
| 4,917,486 | | 4/1990 | Raven et al. . |
| 5,311,224 | * | 5/1994 | Enomoto . |
| 5,342,351 | * | 8/1994 | Blaha et al. . |
| 5,634,923 | * | 6/1997 | Brenner et al. . |
| 5,954,711 | | 9/1999 | Ozaki et al. . |
| 6,110,165 | * | 8/2000 | Ota . |

FOREIGN PATENT DOCUMENTS

| 0 228 778 | 10/1986 | (EP) . |
| 0 356 282 | 7/1989 | (EP) . |
| 0 548 668 A1 | 12/1992 | (EP) . |
| 7-194645 | 8/1995 | (JP) . |
| WO 91/01703 | 2/1991 | (WO) . |

* cited by examiner

Primary Examiner—David M. Shay
(74) Attorney, Agent, or Firm—Finnegan, Henderson, Farabow, Garrett & Dunner, L.L.P.

(57) ABSTRACT

In a laser treatment apparatus, a treatment laser beam emitted from a laser source 10 is coaxially aligned to an aiming beam emitted from an aiming light source 18 by a beam splitter 20. The coaxial beams are delivered to a patient's eye E through a light delivery optical system, when a controller 60 controls an inclination angle of a filter 57 to change its spectral characteristics such that the filter cuts off the treatment laser beam during the treatment laser irradiation, while allows to the aiming beam to pass during the observation of the patient's eye.

9 Claims, 8 Drawing Sheets

LASER TREATMENT APPARATUS

BACKGROUND OF THE INVENTION

1. Field of the Invention

The present invention relates to a laser treatment apparatus for treating an affected part of a patient by irradiating the part with a treatment laser beam emitted from a laser source.

2. Description of Related Art

Conventionally, a laser treatment apparatus for treating an affected part of a patient adjusts a visible aiming beam to the affected part and then emits a treatment laser beam to the aiming part. In a laser apparatus provided with a laser source that emits a visible treatment laser beam, the apparatus being used in ophthalmology and dermatology, the treatment laser source is also used for emitting an aiming beam by reducing the light quantity or another laser source (for example, a semiconductor laser) is provided to emit an aiming beam which is aligned coaxially to the treatment laser beam.

Such the laser apparatus is generally provided with a protector for protecting operator's eyes from reflection laser beams reflected by a lens or patient's eye. If using the aiming beam and the treatment laser beam that have the same color (i.e., substantially the same wavelength region), the conventional treatment apparatus uses a system to insert an operator protection filter on an observation optical path at laser irradiation time, while to move the filter off the observation optical path at patient eye observation time.

However, this filter insertion system causes problems that the operator and the patient could not concentrate their attention on the treatment operation due to frequent inserting and removing operations and noise caused by such the operations.

On the other hand, in a treatment laser apparatus separately provided with a treatment laser source and an aiming light source, which emits an aiming beam having a different wavelength from a treatment laser beam emitted from the treatment laser source, a dichroic mirror is used to protect operator's eyes from the treatment laser beam and allow the operator to observe the aiming beam, without using the operator protection filter insertion system.

However, there are some cases where the difference of wavelengths between the treatment laser beam and the aiming beam causes clinical inconveniences. For example, when a laser beam with a blue or green wavelength is used for a treatment beam, the following problems may occur in an argon laser photocoagulation apparatus using an aiming beam with a red wavelength.

When the fundus diseases treatment is performed on a patient's eye affected with cataract in the crystalline lens or opacities of the vitreous, the red aiming beam is relatively easy to reach the eye fundus, while the blue or green treatment beam tends to scatter in the opacity part and does not sufficiently reach the eye fundus. Thus, the laser photocoagulation can not be achieved or only the insufficient resulting effect can be obtained.

In addition, it is known that the transmittance of the crystalline lens changes with age and it lowers with respect to the visible light of a short wavelength. This case also results in the same problems as in the above case. In such the conditions, if the operator can observe the red aiming beam which less scatters on the fundus of the patient's eye, the operator tends to consider that the laser treatment on the eye fundus can be properly conducted. However, the actual laser treatment result was often insufficient due to the above mentioned reasons.

The red aiming beam having high transmittance deeply reaches the inside of the tissue, while the blue or green treatment laser beam with a shorter wavelength than the red light much scatters and is absorbed in the tissue at a relatively shallow part. Accordingly, there is a case where the actual treatment laser irradiation result does not conform to the operator's intention at the time of observation using the aiming beam.

SUMMARY OF THE INVENTION

The present invention has been made in view of the above circumstances and has an object to overcome the above problems and to provide a laser treatment apparatus capable of satisfactorily performing an operator protecting function against a treatment laser beam, while utilizing advantages resulting from that the treatment laser beam and an aiming beam have substantially the same wavelengths.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for treating an affected part of a patient by irradiating it with a treatment laser beam, the apparatus including an observation optical system for observing the affected part, a treatment laser source which emits a treatment laser beam, an aiming light source which emits an aiming beam of a wavelength approximately equal to a wavelength of the treatment laser beam, a light delivery optical system for delivering the treatment laser beam emitted from the treatment laser source and the aiming beam emitted from the aiming light source to the affected part, a filter for protecting an operator from the treatment laser beam, the filter being disposed on an optical path of the observation optical system, and a device for changing filter spectral characteristics of the filter in relation to wavelength transmittance and absorption between observation of the affected part and irradiation of the treatment laser beam.

According to the above laser treatment apparatus, the filter spectral characteristics changing device acts to shift the spectral characteristics of the filter so that the filter cuts off the treatment laser beam during the treatment laser irradiation and allows the aiming beam to pass during the observation. Specifically, the filter spectral characteristics changing device changes the inclination angle of the filter with respect to the observation optical axis in order to shift the wavelength region of the treatment laser beam that the filter cuts off.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENT

A detailed description of a preferred embodiment of a laser treatment apparatus embodying the present invention will now be given referring to the accompanying drawings. In the present embodiment, the laser treatment apparatus is applied to a laser photocoagulation apparatus (which is simply referred to as a laser apparatus hereinafter).

Figure 1:
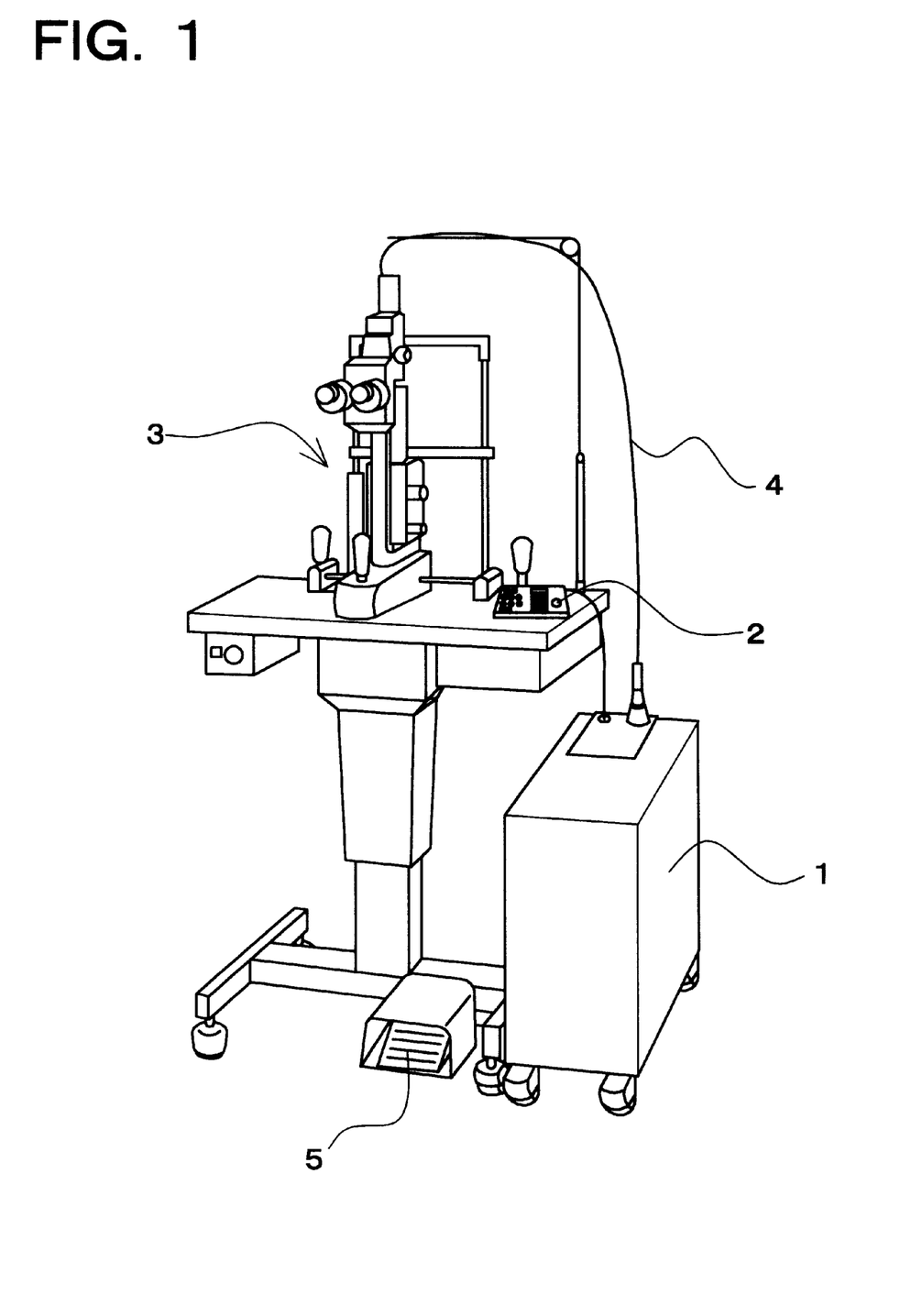
FIG. 1 is a perspective view of a laser photocoagulation apparatus in an embodiment according to the present invention.

In FIG. 1, a laser apparatus is constructed of a laser unit 1, a control box 2 for setting various treatment laser irradiation conditions by manual input operation, a slit lamp delivery 3 which include s an irradiation optical system 30, an illumination optical system 40, an observation optical system 50 and so on, a fiber cable 4 for delivering a treatment laser beam and an aiming beam to the slit lamp delivery 3, and a foot switch 5 for generating a trigger signal to start laser irradiation.

Figure 2:
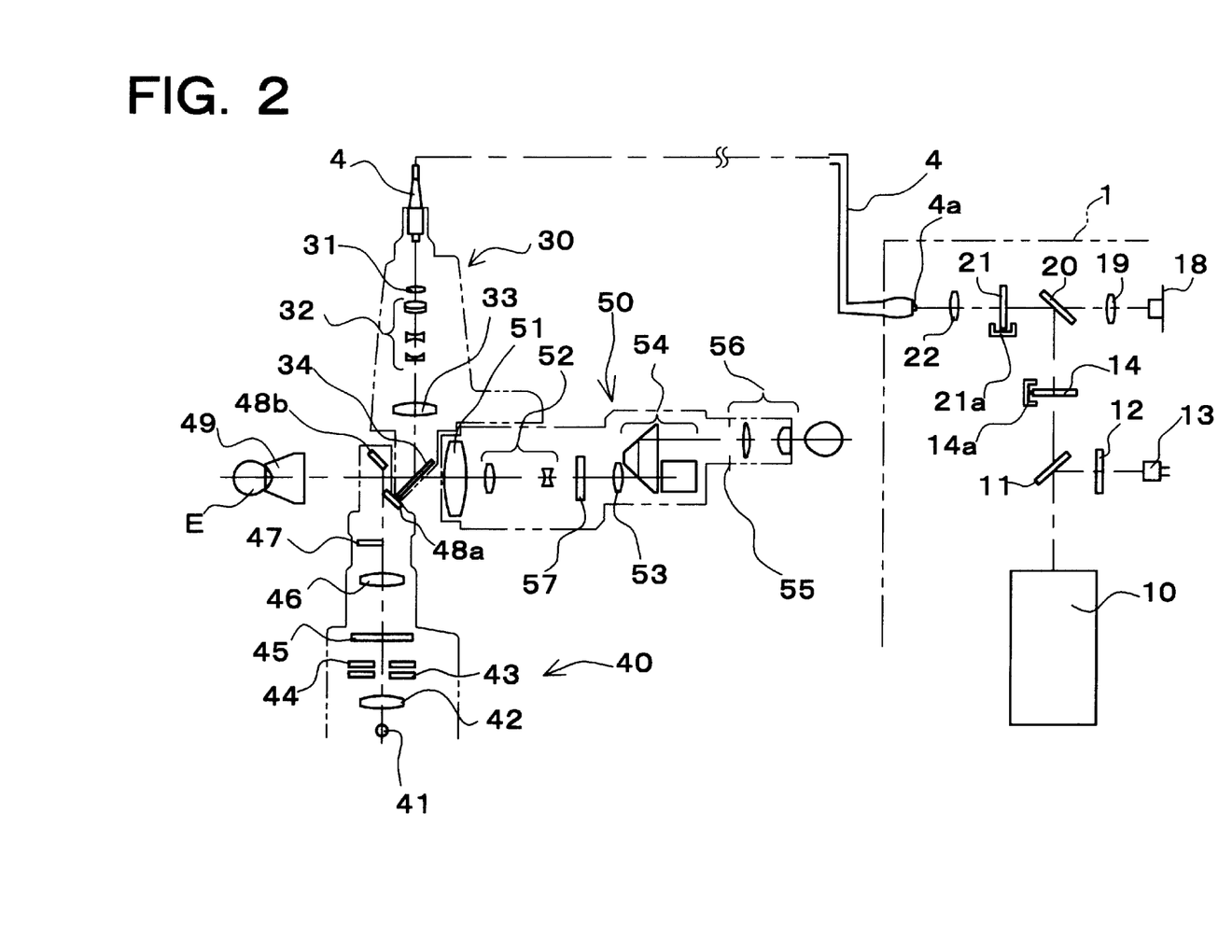
FIG. 2 is a block diagram of an optical system of the laser photocoagulation apparatus in the embodiment.

An optical system of the laser apparatus constructed as above is shown in FIG. 2. Reference numeral 10 indicates a laser source which emits a laser beam for treatment. In the present embodiment, for the laser source 10, an Nd:YAG laser which emits a standard wavelength of 1064 nm is used for producing a linearly polarized green light with a half wavelength (532 nm). A part of the treatment laser beam (simply referred to as a treatment beam hereinafter) emitted from the laser source 10 is allowed to pass through a beam splitter 11. Another part of the treatment beam is reflected by the beam splitter 11 and enters an output sensor 13 through a diffusing plate 12.

Numeral 14 indicates a first safety shutter disposed on the optical path of the treatment beam emitted from the laser source 10. The shutter 14 is moved out of the optical path to allow the treatment beam to pass in response to an instruction of treatment laser irradiation issued by the depression of the foot switch 5, while the shutter 14 is inserted onto the optical path to prevent the passage of the treatment beam when abnormal conditions and so on are encountered. Such the opening and closing motion of the first safety shutter 14 is controlled by a safety shutter driving device 63 which will be mentioned later and sensed by a shutter sensor 14a.

Numeral 18 indicates a semiconductor laser for emitting an aiming beam. This laser 18 in the present embodiment emits a green light like the treatment light. The aiming beam emitted from the semiconductor laser 18 passes through a collimator lens 19 and is coaxially aligned to the treatment beam by a polarized beam splitter 20.

Figure 3:
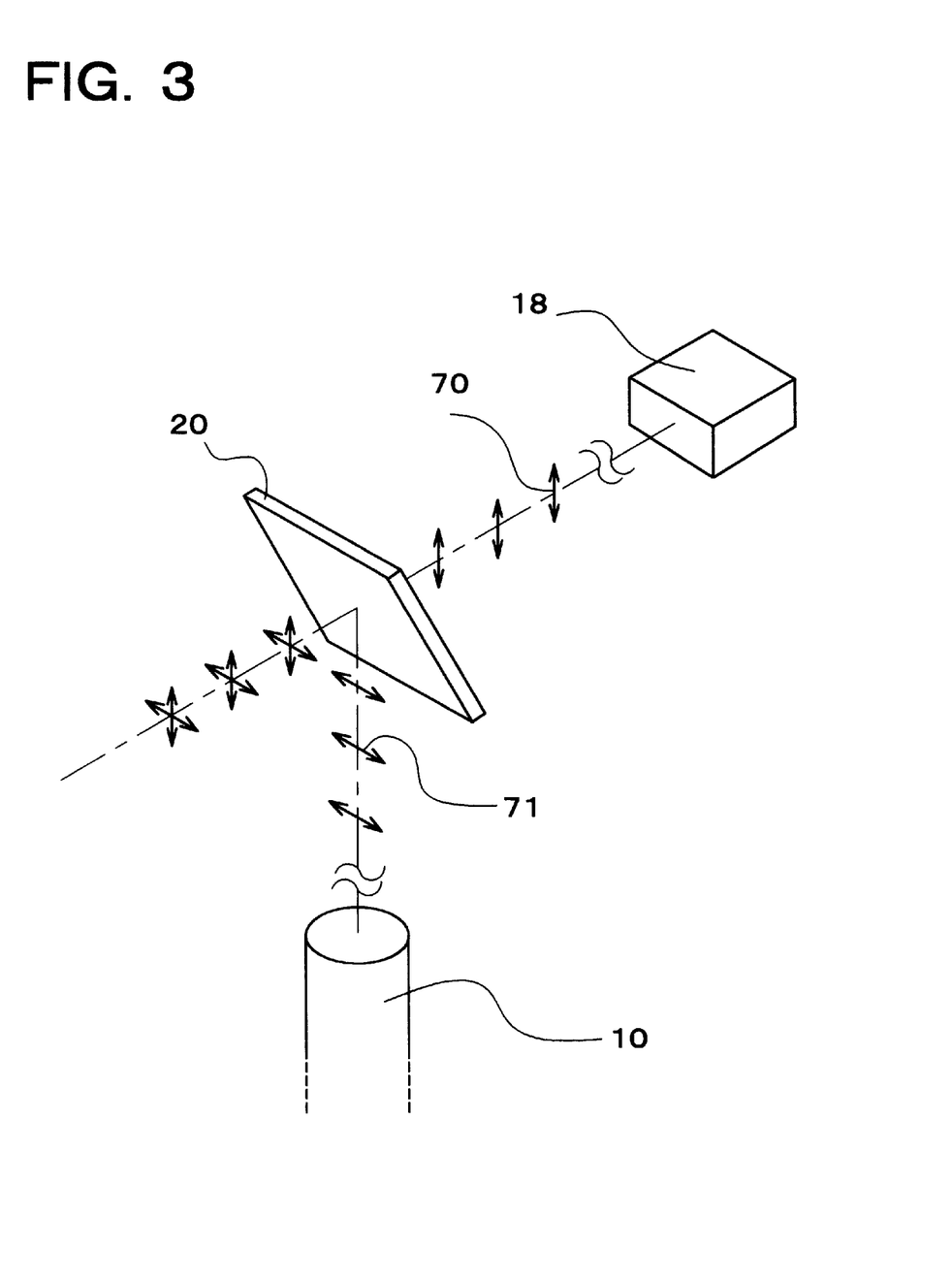
FIG. 3 is an explanatory view showing a method of coaxially aligning a treatment laser beam to an aiming beam.

The relationship between the splitter 20 and each of the laser beams is set in the following. Specifically, the splitter 20 is designed to pass most of the laser (aiming) beam with a linearly polarized light with a polarization plane 70 (i.e., P-polarization-component) emitted from the semiconductor laser 18 and to reflect most of the laser (treatment) beam with a polarization plane (i.e., S-polarization-component) perpendicular to the polarization plane 70. A polarization plane 71 of the treatment beam emitted from the laser source 10 is set to be perpendicular to the polarization plane 70 of the aiming beam passable through the polarized beam splitter 20. Thus, the treatment beam is mostly reflected by the splitter 20 and efficiently coaxially combined with the aiming beam.

Numeral 21 is a second safety shutter, disposed on the optical path of the combined laser beams, for opening and cutting the optical path. This opening and cutting motions of the shutter 21 is sensed by a shutter sensor 21a. Numeral 22 indicates a light condensing lens which condenses the laser beams to an incident plane 4a of the optical fiber 4. The incident laser beams are delivered through the optical fiber 4 to the irradiation optical system 30 of the slit lamp delivery 3.

The irradiation optical system 30 is provided with a collimator lens 31, a variable magnification lens 32 for changing the spot size of the laser beams, an objective lens 33, and a drive mirror 34. This mirror 34 can be flexibly moved to change its reflection angle in response to the operation of a manipulator not shown by the operator. Thus, the irradiation point can be fine adjusted.

The illumination optical system 40 is provided with an illumination light source 41, a condenser lens 42, a variable circular aperture 43, a variable slit plate 44, a filter 45, a projection lens 46, a compensation lens 47, dividing mirrors 48a and 48b, and a contact lens 49. A visible light flux emitted from the light source 41 passes through the condenser lens 42 and then the circular aperture 43 and the slit plate 44 to form a slit-like light flux with the height determined by the aperture 43 and the width determined by the slit plate 44. Thereafter, the slit-like illumination light passes through the filter 45, the projection lens 46, and it is reflected by the dividing mirrors 48a and 48b to the patient's eye E through the contact lens 49.

The observation optical system 50 is provided with an objective lens 51 used in common between the right and left observation optical paths, a variable magnification lens 52, an image forming lens 53, an erect prism 54, a field diaphragm 55, and eye pieces 56. Those components 52–56 are disposed on each of the right and left optical paths. An operator protection filter 57 is disposed between the variable magnification lens 52 and the image forming lens 53 and across both of the right and left optical paths. This filter 57 can be controlled to change its inclination angle with respect to the observation optical axis to thereby change the spectral characteristics which will be mentioned later.

Figure 4:
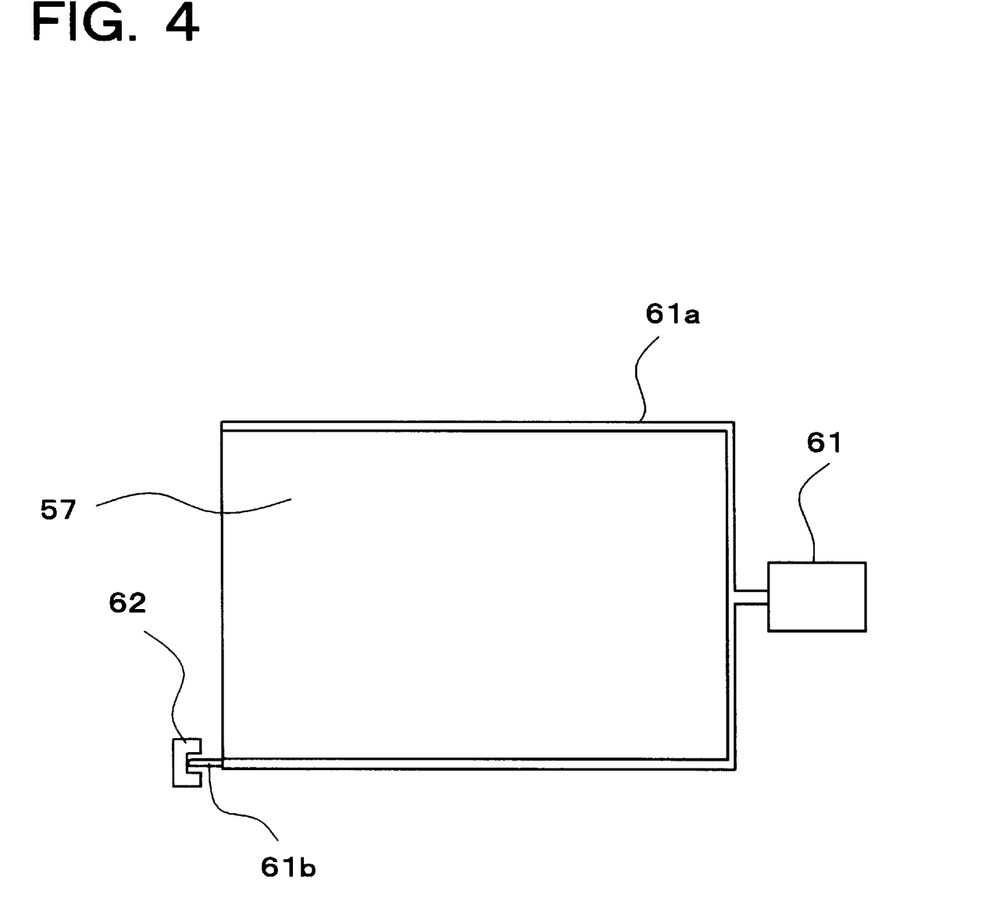
FIG. 4 is a schematic view of a system for driving an operator protection filter in the embodiment.

FIG. 4 schematically shows a system for driving the operator protection filter 57. This filter 57 is fitted in a filter frame 61a connected with a pulse motor 61, and the inclination angle of the filter 57 with respect to the observation optical axis can be changed by the rotation of the motor 61. A light shield plate 61b is fixedly attached to the filter frame 61a. In cooperation of the light shield plate 61b, a photosensor 62 detects the position of the filter 57 when comes to perpendicular to the observation optical axis.

It is to be noted that a piezoelectric element, for example, may be used instead of the pulse motor if minute adjustment of the inclination angle of the filter 57 has to be exactly controlled. Alternatively, if an exact detection of the inclination angle of the filter 57 is needed, a rotary-type potentiometer may be attached to the shaft of the motor 61 or a linear potentiometer may be disposed in contact with the frame 61a to directly detect the movement of the frame 61a. Thus, the filter positional information detected by the above potentiometers is feedback-controlled, so that the filter 57 can be more precisely inclined.

Subsequently, the variation in the spectral characteristics of the operator protection filter 57 in response to the change of the inclination angle is explained. In the present embodiment, as an example of the operator protection filter 57, used was the filter having the characteristics that the transmittance of light with wavelengths in about 500 nm–580 nm became approximately zero when the filter was placed so that a filter plane was made perpendicular (Inclination angle=0) to an optical axis of a parallel light beam incident on the filter. This filter can be manufactured by coating of thirteen layers in the total film number. Specifically, the first layer is made of an $Al_2O_3$ film having a thickness of 268 nm, the second layer is made of a $TiO_2$ film having a thickness of 402 nm, and the third layer is made of an $MgF_2$ film having a thickness of 134 nm. These second and third layers are then alternately repeated four times each to form the $4^{th}$ through $12^{th}$ layers. Finally, the $13^{th}$ layer is made of an $SiO_2$ film having a thickness of 536 nm.

Figure 5:
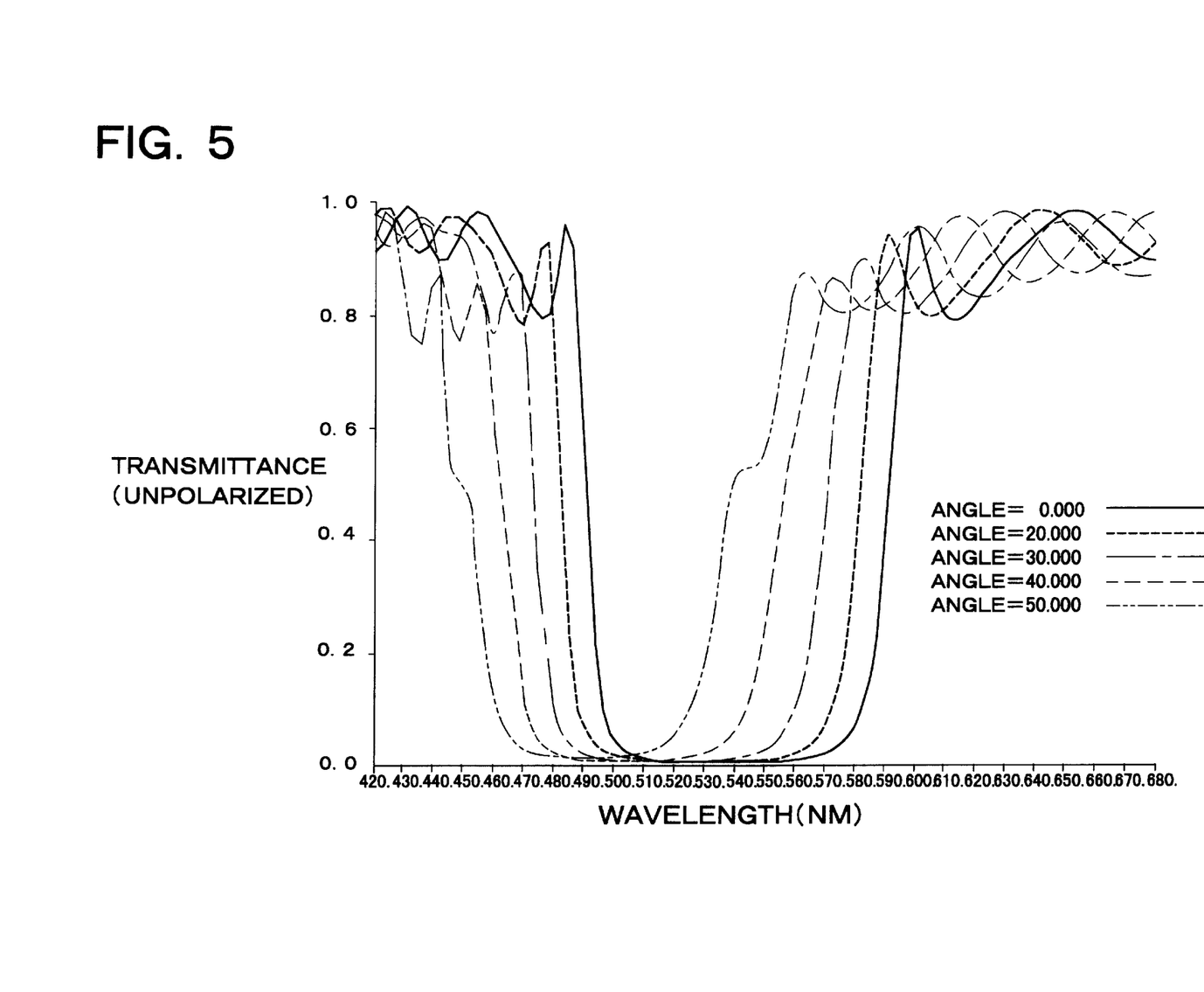
FIG. 5 is a graph showing a change of spectral characteristics by a change of filter angles in the embodiment.

FIG. 5 is a graph showing the change of the spectral characteristics (transmission characteristics) of thus configured filter in relation to the inclination angle. In the graph, the vertical axis indicates transmittance and the horizontal axis indicates wavelength. The spectral characteristics were measured at each inclination angle of 0°, 20°, and 30°. As shown in FIG. 5, at approximately 0° of the filter inclination angle, the wavelength of which transmittance was substantially zero was about 500–580 nm. When the filter inclination angle was changed to 30°, the wavelength was shifted to about 480–560 nm accordingly. By further changing the filter angle to about 50° or more, the filter became able to allow the light with a wavelength of 532 nm to pass.

Accordingly, the filter 57 in the present embodiment has the spectral characteristics of cutting off the treatment beam with the wavelength of 532 nm when the filter is positioned perpendicularly (Inclination angle=0) to the observation optical axis, while allowing the aiming beam (a green light) with substantially the same wavelength (532 nm) as the treatment beam to pass when the filter is inclined at the angle 50°.

In this way, if only changes its inclination angle, the filter 57 as positioned on the observation optical path can cut off the treatment beam and allow the aiming beam with substantially the same wavelength as the treatment laser beam to pass such that the operator can observe the aiming beam.

Figure 6:
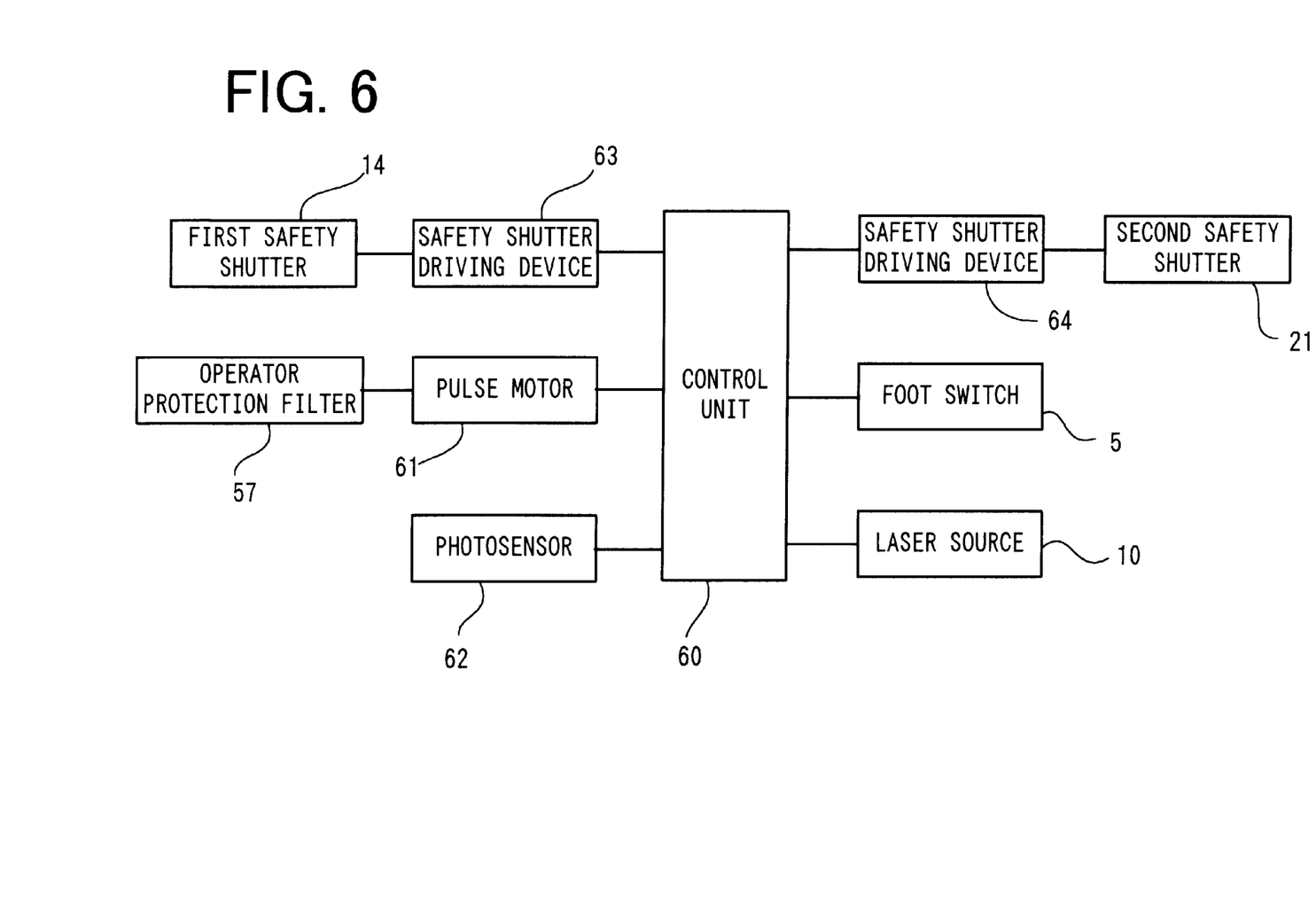
FIG. 6 is a block diagram of a control system of the apparatus in the embodiment.

Next, the operation of the laser apparatus in the embodiment is explained with reference to FIG. 6 showing a schematic block diagram of a control system of the apparatus. To perform laser treatment, switches on the control box 2 are first appropriately operated to set a laser output value, a coagulation condition such as a coagulation time and so on, and a light quantity of the aiming beam. When the aiming beam irradiation is instructed, the control unit 60 drives a safety shutter driving device 64 to move the shutter 21 out of the optical path. The control unit 60 initializes the motor 61 and rotates it to incline the filter 57 by a predetermined angle from the position where the photosensor 62 has detected the light shield plate 61b. The aiming beam reflected by the patient's eye E is thus allowed to pass through the filter 57. The operator can observe the aiming beam through the observation optical system 50.

The operator requests the patient to sit in a predetermined position and hold it, and then operates a joystick and the like to adjust the slit lamp delivery 3 until the slit illumination light is focused on the patient's eye E. After adjustment of the slit light quantity, the operator puts the contact lens 49 on the patient's eye E, and adjusts the aiming beam emitted from the semiconductor laser 18 to the affected part of the patient's eye E with the use of the manipulator not shown while observing the affected part through the observation optical system 50. The aiming beam with the color equal to the color of the treatment beam then behaves like the actual treatment beam in the irradiated part. Thus, by observation prior to treatment beam irradiation, the operator can have grasp and prediction of the possible problems caused by the treatment beam irradiation, such as propriety of the execution of the laser photocoagulation, and degree of the effect. It is therefore easy for the operator to take appropriate action in advance in order to reduce a difference between the intended result and the actual result.

Upon completion of adjustment of the aiming beam, the operator depresses the foot switch 5 to start laser irradiation. When the foot switch 5 is depressed, a trigger signal for instructing the laser irradiation is transmitted to the control unit 60. In response to the trigger signal, the control unit 60 rotates the motor 61 to arrange the filter 57 so as to be perpendicular to the observation optical axis. Whether or not the filter 57 has been precisely arranged is detected by a signal from the photosensor 62. When the control unit 60 detects that the filter 57 has been arranged in a proper position, it drives the laser source 10 to emit the treatment beam while drives the driving device 63 to move the shutter 14 out of the optical path.

The treatment beam from the laser source 10 is reflected by the polarized beam splitter 20, then coaxially aligned to the aiming beam, and delivered to the patient's eye E through the irradiation optical system 30. Although the reflection light from the patient's eye E and others enters the observation optical system 50, it is cut off by the filter 57 being arranged perpendicularly to the observation optical axis. The operator's eyes can thus be protected from the treatment beam.

As described in detail, the laser treatment apparatus in the embodiment can satisfactorily perform an operator protecting function against the treatment laser beam, while utilizing advantages resulting from that the treatment laser beam and an aiming beam have substantially the same wavelengths.

The present invention may be embodied in other specific forms without departing from the spirit or essential characteristics thereof.

Figure 8:
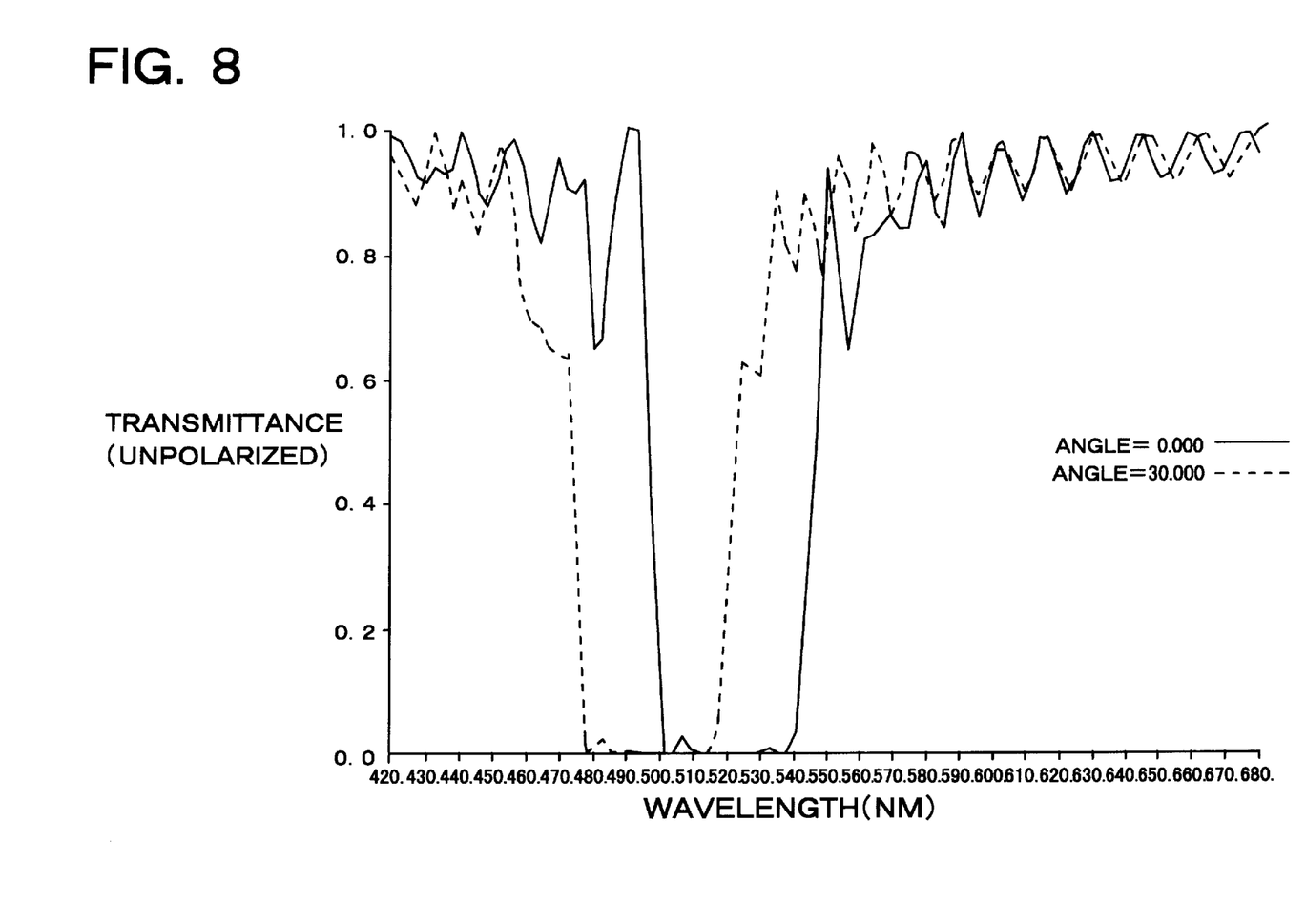
FIG. 8 is a graph showing a change of spectral characteristics by a change of filter angles in a modified example in which the filter differs in configuration from the filter mentioned in FIG. 5.

For instance, filters having different coated layers from those mentioned in relation to FIG. 5 may be used. One of the filters can be manufactured by coating of thirty-two layers in the total film number. Specifically, the first layer is made of a $TiO_2$ film having a thickness of 390 nm and the second layer is made of an $SiO_2$ film having a thickness of 390 nm. These first and second layers are then alternately repeated fourteen times each to form the $3^{rd}$ through $30^{th}$ layers, and the $31^{st}$ layer is made of a $TiO_2$ film having a thickness 390 nm and the $32^{nd}$ layer is made of an $SiO_2$ film having a thickness of 260 nm. In an examination using the thus constructed filter, as shown in FIG. 8, the wavelength of which transmittance was substantially zero was about 500–540 nm when the filter inclination angle was approximately 0°, and the wavelength was shifted to about 480–515 nm as the filter inclination angle was changed to 30°.

Furthermore, in the above embodiment, to coaxially align the treatment light to the aiming beam with the color equal to the color of the treatment beam, each of the treatment laser source and the aiming light source is configured to emit a linearly polarized light. Alternatively, an optical system shown in FIG. 7 may be used in the case of using the light that is not linearly polarized light. In the optical system, two light flux, i.e., the treatment beam and the aiming beam are incident on the identical optical fiber and coaxially aligned at an exit plane of the fiber.

Figure 7:
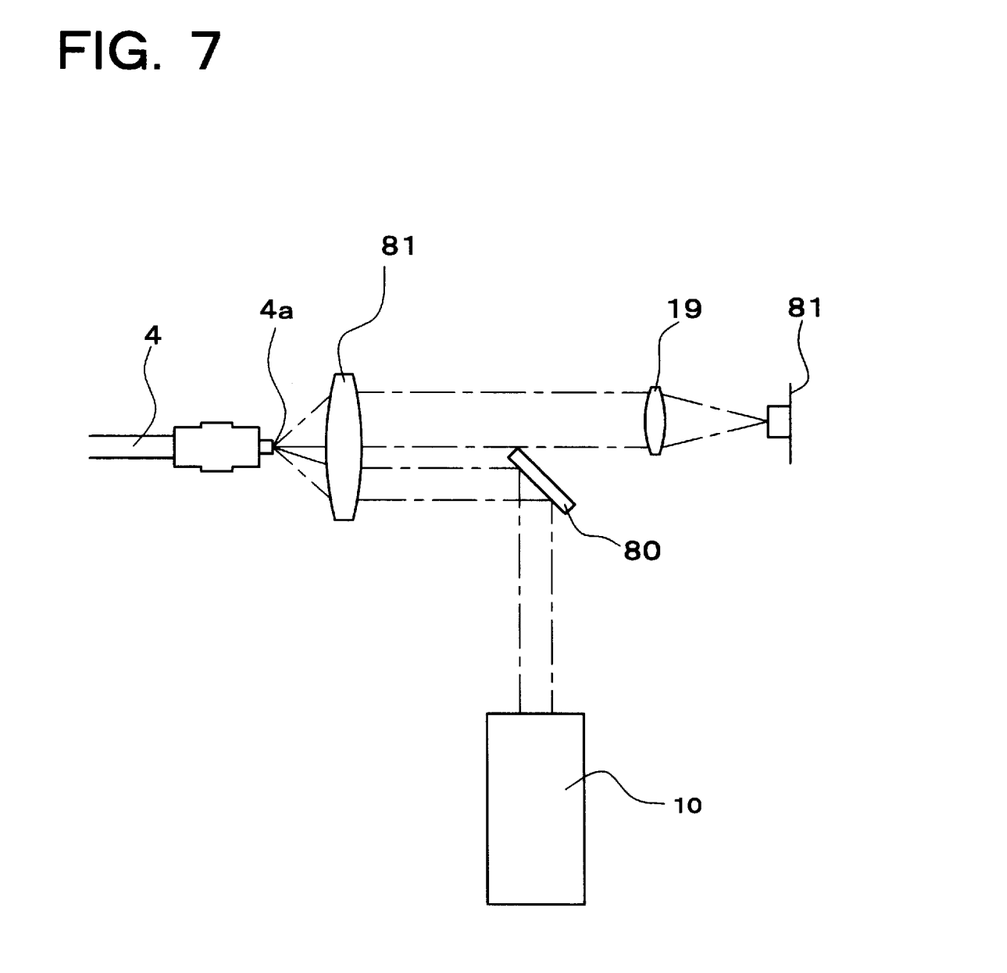
FIG. 7 is a schematic view of an optical system for coaxially aligning two light fluxes which are not linearly polarized lights.

Specifically, the aiming beam emitted from the semiconductor laser 18 as shown in FIG. 7 is made into parallel light flux by the collimator lens 19 and condensed by a condensing lens 81 to the incident plane 4a of the optical fiber 4. On the other hand, the treatment beam emitted from the laser source 10 is reflected by a full-reflection mirror 80 and condensed by the lens 81 to the incident plane 4a. In this way, the two light flux which have different optical axes are allowed to enter the optical fiber 4 through the lens 81 and coaxially combined at the exit plane of the optical fiber 4.

A polarizer and the like may be used to previously select a polarizing direction so that the two light flux, even if they are not linearly polarized light, may be coaxially aligned by the polarized beam splitter 20. Besides, a movable mirror removably disposed on the optical path and a sector-shaped rotary mirror may be used instead of the polarized beam splitter 20. In this case, by those mirrors inserted on the optical path during treatment laser irradiation, the treatment beam and the aiming beam having substantially the same wavelength are efficiently aligned coaxially to each other.

For the treatment laser source, instead of the Nd:YAG laser used in the above embodiment, an argon laser which emits laser beams with wavelengths of 488 nm and 514.5 nm respectively or a krypton laser which emits laser beams with plural wavelengths may be used. In the case of the laser apparatus which emits the treatment beams with plural wavelengths, aiming light sources are provided in correspondence with the colors of the treatment beams and an operator protection filter capable of absorbing each of the wavelengths is used. The spectral characteristics of the protection filter are changed in accordance with the inclination angle thereof. Thus, the laser beams for treatment and for aiming can be coaxially aligned to each other.

If the absorbing efficiency to each of the wavelengths is insufficient due to a single inclination angle, the inclination angle may be changed in correspondence with the wavelengths respectively. If the single filter is not enough to absorb all the wavelengths, furthermore, the number of filters may be increased as necessary.

In addition, if the filter is disposed at a position where the observation optical axis may be shifted due to the change of the inclination angle of the filter, two filters may be used to adjust the observation optical axis so as not to shift.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for treating an affected part of a patient by irradiating it with a treatment laser beam, the apparatus including:
   an observation optical system for observing the affected part;
   a treatment laser source which emits a treatment laser beam;
   an aiming light source which emits an aiming beam of a wavelength approximately equal to a wavelength of the treatment laser beam;
   a light delivery optical system for delivering the treatment laser beam emitted from the treatment laser source and the aiming beam emitted from the aiming light source to the affected part;
   a filter disposed on an optical path of the observation optical system; and
   a changing device which changes a wavelength transmittance characteristic of the filter by changing an inclination angle of the filter with respect to an optical axis of the observation optical system.

2. The laser treatment apparatus according to claim 1, wherein the changing device changes the wavelength transmittance characteristics of the filter so that the filter transmits the wavelength of the treatment laser beam and the aiming beam when the treatment laser beam is not irradiated, but does not transmit the wavelength of the treatment laser beam and the aiming beam when the treatment laser is irradiated.

3. The laser treatment apparatus according to claim 1, wherein the wavelength of the treatment laser beam and the aiming beam is not transmitted when the filter is disposed perpendicularly to the optical axis of the observation optical system by the changing device, but is transmitted when the filter is disposed at a predetermined inclination angle to the optical axis.

4. The laser treatment apparatus according to claim 1, further including:
   an input device for inputting a trigger signal to start irradiation of the treatment laser beam from the treatment laser source; and
   a controller which controls the changing device in response to input of the trigger signal.

5. The laser treatment apparatus according to claim 1, wherein the changing device includes a motor which rotates the filter to change the inclination thereof.

6. The laser treatment apparatus according to claim 1 further including a filter angle detection device which detects the inclination angle of the filter.

7. The laser treatment apparatus according to claim 6, further including a controller which controls irradiation of the treatment laser beam based on the detection result by the filter angle detection device.

8. The laser treatment apparatus according to claim 1, wherein the light delivery optical system includes a member for coaxially aligning the treatment laser beam emitted from the treatment laser source and the aiming beam emitted from the aiming light source to each other.

9. The laser treatment apparatus according to claim 8, wherein the coaxial aligning member includes a light condensing optical member for condensing the treatment laser beam and the aiming beam to coaxially align the beams.

* * * * *